United States Patent
D'Alessio et al.

(10) Patent No.: US 12,020,789 B1
(45) Date of Patent: Jun. 25, 2024

(54) SYSTEMS AND METHODS ENABLING BASELINE PREDICTION CORRECTION

(71) Applicant: Unlearn.AI, Inc., San Francisco, CA (US)

(72) Inventors: Luca D'Alessio, Medford, MA (US); Rishabh Gupta, Somerville, MA (US); Charles Kenneth Fisher, Truckee, CA (US)

(73) Assignee: Unlearn.AI, Inc., San Francisco, CA (US)

( * ) Notice: Subject to any disclaimer, the term of this patent is extended or adjusted under 35 U.S.C. 154(b) by 0 days.

(21) Appl. No.: 18/340,715

(22) Filed: Jun. 23, 2023

Related U.S. Application Data (60) Provisional application No. 63/485,771, filed on Feb. 17, 2023.

(51) Int. Cl.
  *G06N 3/02* (2006.01)
  *G16H 10/60* (2018.01)

(52) U.S. Cl.
  CPC .............. *G16H 10/60* (2018.01); *G06N 3/02* (2013.01)

(58) Field of Classification Search
  CPC ........ G06N 3/02; G06N 3/047; G06N 3/0475; G06N 20/00
  See application file for complete search history.

(56) References Cited

U.S. PATENT DOCUMENTS

| 7,634,464 B2 | 12/2009 | Chen et al. |
| 8,150,629 B2 | 4/2012 | Geerts et al. |
| 9,495,582 B2 | 11/2016 | Guissin et al. |

(Continued)

FOREIGN PATENT DOCUMENTS

| CA | 3088204 A1 | 7/2019 |
| CN | 111758108 A | 10/2020 |

(Continued)

OTHER PUBLICATIONS

Fisher et al., "Machine Learning for Comprehensive Forecasting of Alzheimer's Disease Progression", Sep. 20, 2019, Scientific Reports, pp. 1-41. (Year: 2019).*

(Continued)

*Primary Examiner* — Paulinho E Smith
(74) *Attorney, Agent, or Firm* — KPPB LLP

(57) ABSTRACT

Systems and techniques for time-series forecasting are illustrated. One embodiment includes a method for refining time-series forecasts, the method obtains timestep information including baseline information, a time gap, and context information. The baseline information includes information known about the system at a time when the multivariate time-series is generated. The context information includes at least one vector of time-independent background variables related to the system. The method determines, based on the timestep information, parameter predictions for the system at a first timestep and a second timestep. The method derives actual state values for the system at the first timestep. The method updates the parameter predictions for the system at the second timestep, using a gating function, based on a discrepancy between: the parameter predictions for the system at the first timestep, and the actual state values for the system at the first timestep.

20 Claims, 4 Drawing Sheets

(56) References Cited

U.S. PATENT DOCUMENTS

| | | |
|---|---|---|
| 10,398,389 B1 | 9/2019 | D'Alessandro et al. |
| 10,650,929 B1 | 5/2020 | Beck et al. |
| 10,726,954 B2 | 7/2020 | Su et al. |
| 11,120,528 B1 | 9/2021 | Seely et al. |
| 11,196,656 B1* | 12/2021 | Jain ................ H04L 41/0893 |
| 11,200,511 B1 | 12/2021 | London |
| 11,501,429 B2 | 11/2022 | Stamatoyannopoulos et al. |
| 11,574,462 B1 | 2/2023 | Bhatia et al. |
| 11,610,126 B1* | 3/2023 | Heckerman ............ G06N 20/10 |
| 11,636,309 B2 | 4/2023 | Fisher et al. |
| 11,868,900 B1 | 1/2024 | Smith et al. |
| 11,966,850 B1 | 4/2024 | Smith et al. |
| 2004/0059696 A1 | 3/2004 | Kropaczek et al. |
| 2004/0193019 A1 | 9/2004 | Wei |
| 2005/0047646 A1 | 3/2005 | Jojic et al. |
| 2005/0080462 A1 | 4/2005 | Jenkins et al. |
| 2008/0082359 A1 | 4/2008 | Jung et al. |
| 2009/0326976 A1 | 12/2009 | Morris |
| 2010/0235310 A1 | 9/2010 | Gage et al. |
| 2010/0254973 A1 | 10/2010 | Mohapatra et al. |
| 2011/0116522 A1* | 5/2011 | Riggs ................ G03F 7/70575 372/32 |
| 2011/0218817 A1 | 9/2011 | Spiegel |
| 2013/0311968 A1* | 11/2013 | Sharma ............... G06F 11/3692 717/101 |
| 2014/0019059 A1 | 1/2014 | Shankle et al. |
| 2014/0046683 A1 | 2/2014 | Michelson et al. |
| 2014/0257128 A1 | 9/2014 | Moxon et al. |
| 2014/0279777 A1 | 9/2014 | Cornebise et al. |
| 2015/0010610 A1 | 1/2015 | Tom et al. |
| 2015/0185716 A1* | 7/2015 | Wichmann ................ F02C 9/28 700/287 |
| 2016/0140300 A1 | 5/2016 | Purdie et al. |
| 2016/0180053 A1 | 6/2016 | Fuertinger et al. |
| 2016/0217384 A1* | 7/2016 | Leonard ................ G06N 5/022 |
| 2016/0222448 A1 | 8/2016 | Horvath |
| 2017/0091615 A1* | 3/2017 | Liu ........................ G06N 3/044 |
| 2017/0161635 A1 | 6/2017 | Oono et al. |
| 2017/0255871 A1 | 9/2017 | Macready et al. |
| 2017/0286627 A1 | 10/2017 | Barhak |
| 2017/0344706 A1 | 11/2017 | Torres et al. |
| 2017/0357844 A1 | 12/2017 | Comaniciu et al. |
| 2017/0364043 A1* | 12/2017 | Ganti ..................... G05B 17/02 |
| 2017/0364803 A1* | 12/2017 | Calmon ................ G06N 3/045 |
| 2017/0372193 A1 | 12/2017 | Mailhe et al. |
| 2018/0018590 A1 | 1/2018 | Szeto et al. |
| 2018/0046780 A1 | 2/2018 | Graiver et al. |
| 2018/0081914 A1 | 3/2018 | Zoll et al. |
| 2018/0082172 A1 | 3/2018 | Patel et al. |
| 2018/0150728 A1 | 5/2018 | Vahdat |
| 2018/0204138 A1 | 7/2018 | Nugent |
| 2018/0299152 A1* | 10/2018 | Libal .................... H04W 4/021 |
| 2018/0314573 A1* | 11/2018 | Chang ................... G06N 20/00 |
| 2018/0315505 A1 | 11/2018 | Itu et al. |
| 2018/0316781 A1* | 11/2018 | Salem ................... H04L 67/306 |
| 2018/0336319 A1 | 11/2018 | Itu et al. |
| 2019/0018933 A1 | 1/2019 | Oono et al. |
| 2019/0019570 A1 | 1/2019 | Fuertinger et al. |
| 2019/0130281 A1* | 5/2019 | Yang ..................... G06N 3/044 |
| 2019/0220733 A1 | 7/2019 | Fisher et al. |
| 2019/0244680 A1 | 8/2019 | Rolfe et al. |
| 2019/0283247 A1* | 9/2019 | Chang .................. A61B 5/1121 |
| 2019/0303471 A1 | 10/2019 | Lee et al. |
| 2019/0303798 A1* | 10/2019 | Xie ........................ G06Q 50/01 |
| 2020/0035362 A1 | 1/2020 | Abou et al. |
| 2020/0143498 A1* | 5/2020 | Alkan ................ G06Q 50/2057 |
| 2020/0357490 A1 | 11/2020 | Kartoun et al. |
| 2020/0395103 A1 | 12/2020 | Ramakrishnan et al. |
| 2020/0401916 A1 | 12/2020 | Rolfe et al. |
| 2020/0411199 A1 | 12/2020 | Shrager et al. |
| 2021/0057108 A1* | 2/2021 | Fisher .................... G16H 50/20 |
| 2021/0090694 A1 | 3/2021 | Colley et al. |
| 2021/0117842 A1 | 4/2021 | Smith et al. |
| 2021/0158906 A1 | 5/2021 | Xie et al. |
| 2021/0225511 A1 | 7/2021 | Kiraly et al. |
| 2021/0241139 A1* | 8/2021 | Jain ........................ G16H 20/40 |
| 2021/0241860 A1 | 8/2021 | Bhattacharya et al. |
| 2021/0256453 A1* | 8/2021 | Morgan ........ G06Q 10/063112 |
| 2021/0353203 A1 | 11/2021 | Burman et al. |
| 2021/0383173 A1 | 12/2021 | Laaser |
| 2022/0003894 A1* | 1/2022 | Shapiro .................... G01W 1/10 |
| 2022/0051796 A1* | 2/2022 | Zhu ........................ G06N 3/045 |
| 2022/0121955 A1 | 4/2022 | Chavoshi et al. |
| 2022/0157413 A1* | 5/2022 | Fisher .................... G16H 10/20 |
| 2022/0172085 A1 | 6/2022 | Fisher et al. |
| 2022/0187776 A1 | 6/2022 | Bagne |
| 2022/0188601 A1* | 6/2022 | Adler ..................... G06N 3/044 |
| 2022/0262106 A1 | 8/2022 | Khoreva et al. |
| 2022/0300329 A1* | 9/2022 | Abhishek Raja ....... G06F 9/505 |
| 2022/0318689 A1 | 10/2022 | Li-Bland et al. |
| 2022/0344009 A1* | 10/2022 | Schuler da Costa Ferro ............. G16H 10/20 |
| 2022/0410385 A1* | 12/2022 | Shimura ................ B25J 9/1664 |
| 2022/0415454 A1 | 12/2022 | Schuler da Costa et al. |
| 2023/0004796 A1 | 1/2023 | Mayer et al. |
| 2023/0118864 A1* | 4/2023 | Zhang .................... G06V 20/80 382/103 |
| 2023/0209035 A1 | 6/2023 | Kaabi et al. |
| 2023/0245258 A1* | 8/2023 | Ma ........................ G06N 5/022 705/328 |
| 2023/0245777 A1 | 8/2023 | Foschini et al. |
| 2024/0013525 A1 | 1/2024 | Lim et al. |

FOREIGN PATENT DOCUMENTS

| | | | |
|---|---|---|---|
| CN | 112863622 A | 5/2021 | |
| CN | 113724806 A | 11/2021 | |
| EP | 3740908 A1 | 11/2020 | |
| EP | 4018394 A1 | 6/2022 | |
| EP | 4220650 A1 | 8/2023 | |
| EP | 4256418 A2 | 10/2023 | |
| HK | 40098681 A | 4/2024 | |
| JP | 2021511584 A | 5/2021 | |
| JP | 202231730 A | 2/2022 | |
| JP | 2022544859 A | 10/2022 | |
| JP | 7305656 B2 | 6/2023 | |
| JP | 2023551514 A | 12/2023 | |
| WO | WO-0229556 A2 * | 4/2002 | ........... G06F 9/3848 |
| WO | 2006084196 A2 | 8/2006 | |
| WO | 2007022020 A2 | 2/2007 | |
| WO | 2007022020 A3 | 6/2007 | |
| WO | WO-2014114295 A1 * | 7/2014 | ............. F03D 13/20 |
| WO | 2016145379 A1 | 9/2016 | |
| WO | 2019143737 A1 | 7/2019 | |
| WO | WO-2020115487 A1 * | 6/2020 | ........... G06N 3/0445 |
| WO | 2020154573 A1 | 7/2020 | |
| WO | 2021041128 A1 | 3/2021 | |
| WO | 2021077097 A1 | 4/2021 | |
| WO | WO-2022003528 A1 * | 1/2022 | ............. G06F 21/32 |
| WO | 2022101809 A1 | 5/2022 | |
| WO | 2022120350 A2 | 6/2022 | |
| WO | WO-2022125806 A1 * | 6/2022 | ............. A61B 5/0006 |
| WO | 2022120350 A3 | 8/2022 | |
| WO | 2022187064 A1 | 9/2022 | |
| WO | WO-2022210425 A1 * | 10/2022 | |
| WO | 2022272308 A1 | 12/2022 | |
| WO | WO-2022261420 A1 * | 12/2022 | |
| WO | 2019143737 A8 | 3/2023 | |

OTHER PUBLICATIONS

Duan et al, "Utilizing dynamic treatment information for MACE prediction of acute coronary syndrome", 2019, BMC Medical Informatics and Decision Making, pp. 1-11 (Year: 2019).*

Lim et al., "Time-Series Forecasting with Deep Learning: A Survey", Jul. 28, 2021, The Royal Society Publishing, pp. 1-14 (Year: 2021).*

Nguyen et al., "Latent Patient Profile Modelling and Applications with Mixed-Variate Restricted Boltzmann Machine", Advances in Knowledge Discovery and Data Mining, 2013, pp. 123-135.

Nguyen et al., "Supervised Restricted Boltzmann Machines", UAI, 2017, 10 pgs.

(56) References Cited

OTHER PUBLICATIONS

Niu et al., "A review on the attention mechanism of deep learning", Neurocomputing, vol. 452, 2021, pp. 48-62, https://doi.org/10.1016/j.neucom.2021.03.091.

Openai, "Gpt-4 technical report", arXiv preprint arXiv:2303.08774, 2023, 100 pgs.

Overhage et al., "Desideratum for evidence based epidemiology", Drug Safety, 2013, vol. 36, Suppl. 1, pp. S5-S14, DOI: 10.1007/s40264-013-0102-2.

Quinn et al., "Docosahexaenoic Acid Supplementation and Cognitive Decline in Alzheimer Disease: A Randomized Trial", Journal of the American Medical Association, Nov. 3, 2010, vol. 304, No. 17, pp. 1903-1911, doi: 10.1001/jama.2010.1510.

Rogers et al., "Combining patient-level and summary-level data for Alzheimer's disease modeling and simulation: a beta regression meta-analysis", Journal of Pharmacokinetics and Pharmacodynamics, vol. 39, 2012, pp. 479-498.

Romano et al., "Resurrecting weighted least squares", Journal of Econometrics, 197(1), 48 pgs, Available at: https://doi.org/10.1016/j.jeconom.2016.10.003.

Rombach et al., "High-Resolution Image Synthesis with Latent Diffusion Models", arXiv preprint arXiv:2112.10752, 2022, 45 pgs.

Romero et al., "The coalition against major diseases: developing tools for an integrated drug development process for alzheimer's and parkinson's diseases", Clinical Pharmacology & Therapeutics, Aug. 12, 2009, vol. 86, No. 4, pp. 365-367, https://doi.org/10.1038/clpt.2009.165.

Rosen et al., "A New Rating Scale for Alzheimer's Disease", American Journal of Psychiatry, vol. 141, Issue 11, Nov. 1984, pp. 1356-1364, https://doi.org/10.1176/ajp.141.11.1356.

Royston, "A Combined Test for a Generalized Treatment Effect in Clinical Trials with a Time-to-Event Outcome", The Stata Journal, vol. 17, No. 2, 2017 pp. 405-421.

Royston et al., "A Simulation Study Comparing the Power of Nine Tests of the Treatment Effect in Randomized Controlled Trials with a Time-to-Event Outcome", Royston and Parmar Trials, vol. 21, No. 315, 17 pgs. Retrieved on Aug. 14, 2022. Retrieved from <URL: https://link.springer.com/content/pdf/10.1186/s13063-020-4153-2.pdf> entire document.

Royston et al., "Augmenting the Logrank Test in the Design of Clinical Trials in which Non-Proportional Hazards of the Treatment Effect may be Anticipated", Royston and Parmar BMC Medical Research Methodology, vol. 16, No. 16, 2016, 13 pgs. Retrieved on Aug. 14, 2022. Retrieved from <URL:https://bmcmedresmethodol.biomedcentral.conn/track/pdf/10.1186/s12874-016-0110-x.pdf> entire document.

Rubin, "Causal Inference Using Potential Outcomes: Design, Modeling, Decisions", Journal of the American Statistical Association, vol. 100, No. 469, Mar. 2005, pp. 322-331, https://doi.org/10.1198/016214504000001880.

Saharia et al., "Photorealistic text-to-image diffusion models with deep language understanding", arXiv preprint arXiv:2205.11487, 2022, 46 pgs.

Salakhutdinov et al., "Deep boltzmann machines", Proceedings of Machine Learning Research, vol. 5, Apr. 2009, pp. 448-455.

Schuler et al., "Increasing the efficiency of randomized trial estimates via Linear Adjustment for a prognostic score", The International Journal of Biostatistics, vol. 18, No. 2, 2021, pp. 329-356. Available at: https://doi.org/10.1515/ijb-2021-0072.

Shan et al., "Accurate Unconditional p-Values for a Two-Arm Study with Binary Endpoints", Journal of Statistical Computation and Simulation, [Online] Apr. 13, 2018, vol. 88, No. 6, pp. 1200-1210, XP093073190, ISSN: 0094-9655, DOI: 10.1080/00949655.2018.1425690, Retrieved from the Internet: URL:https://www.ncbi.nlm.nih.gov/pmc/artic les/PMC6510515/pdf/nihms-1504617.pdf> [retrieved Jan. 28, 2018].

Shan et al., "Exact p-Values for Simon's Two-Stage Designs in Clinical Trials", Statistics in Biosciences, Springer US,Boston, [Online]Jun. 16, 2016, vol. 8, No. 2, pp. 351-357, XP036062971,ISSN: 1867-1764, DOI:10.1007/S12561-016-9152-1, Retrieved from the Internet: URL:https://www.ncbi.nlm.nih.gov/pmc/artic les/PMC5167475/>.

Silva et al., "Predicting In-Hospital Mortality of ICU Patients: The PhysioNet/Computing in Cardiology Challenge 2012", Computing in Cardiology, 2012, vol. 39, pp. 245-248.

Sohl-Dickstein et al., "Deep Unsupervised Learning using Nonequilibrium Thermodynamics", arXiv preprint arXiv:1503.03585, 2015, 18 pgs.

Song et al., "Generative Adversarial Learning of Markov Chains", Accessed at URL https://openreview.net/forum?id=S1L-hCNtl, 2017, 8 Pgs.

Sox et al., "The Methods of Comparative Effectiveness Research", Annual Review of Public Health, Apr. 2012, vol. 33, pp. 425-445, doi: 10.1146/annurev-publhealth-031811-124610.

Sterne et al., "Multiple imputation for missing data in epidemiological and clinical research: potential and pitfalls", BMJ, 2009, 14 pages, doi: https://doi.org/10.1136/bmj.b2393 (Published Jun. 29, 2009).

Sutskever et al., "The Recurrent Temporal Restricted Boltzmann Machine", Advances in Neural Information Processing Systems, 2009, pp. 1601-1608.

Tan et al., "A tensor-based method for missing traffic data completion", Transportation Research Part C: Emerging Technologies, vol. 28, 2013, pp. 15-27, https://doi.org/10.1016/j.trc.2012.12.007.

Taylor et al., "Factored conditional restricted boltzmann machines for modeling motion style", In Proceedings of the 26th Annual International Conference on Machine Learning, Association for Computing Machinery, 2009, pp. 1025-1032.

Taylor et al., "Modeling human motion using binary latent variables", In Advances in Neural Information Processing Systems, 2007, pp. 1345-1352.

Tieleman, "Training restricted boltzmann machines using approximations to the likelihood gradient", In Proceedings of the 25th international conference on Machine learning, AC Association for Computing Machinery, 2008, pp. 1064-1071.

Tipirneni et al., "Self-supervised transformer for sparse and irregularly sampled multivariate clinical time-series", ACM Transactions on Knowledge Discovery from Data (TKDD), 2022, vol. 1, No. 1, 18 pgs.

Tran et al., "Mixed-Variate Restricted Boltzmann Machines", Asian Conference on Machine Learning, JMLR: Workshop and Conference Proceedings, vol. 20, 2011, pp. 213-229.

Tuzman, Karen Tkach "Broadening role for external control arms in clinical trials", Biocentury, Tools & Techniques, reprint from Jul. 15, 2019, 5 pgs.

Upadhya et al., "Learning Gaussian-Bernoulli RBMs using Difference of Convex Functions Optimization", IEEE Transactions on Neural Networks and Learning Systems, vol. 33, No. 10, 2022, pp. 1-24.

Vaswani et al., "Attention Is All You Need", arXiv preprint arXiv:1706.03762, 2023, 15 pgs.

Ventz et al., "Design and Evaluation of an External Control Arm Using Prior Clinical Trials and Real-World Data", Clincal Cancer Research, vol. 25, pp. 4993-5001; doi: 10.1158/1078-0432.CCR-19-0820.

Yi et al., "ST-MVL: Filling Missing Values in Geo-Sensory Time Series Data", Proceedings of the Twenty-Fifth International Joint Conference on Artificial Intelligence, 2016, pp. 2704-2710.

Yu et al., "Assessment and adjustment of approximate inference algorithms using the law of total variance", arXiv preprint arXiv:1911.08725, Nov. 2019 [online], [retrieved on Jan. 31, 2022], 29 pgs.

Zhang et al., "Predictive Deep Boltzmann Machine for Multiperiod Wind Speed Forecasting", IEEE Transactions on Sustainable Energy, 2015, vol. 6, Issue 4, pp. 1416-1425, doi: 10.31109/TSTE.2015.244387.

Zhu et al., "Physics-Constrained Deep Learning for High-dimensional Surrogate Modeling and Uncertainty Quantification without Labeled Data", arXiv preprint arXiv:1901.06314, 2019, 15 pgs.

Extended European Search Report for European Application No. 19741291.9, Search completed Sep. 8, 2021, dated Sep. 17, 2021, 12 pgs.

(56) References Cited

OTHER PUBLICATIONS

Extended European Search Report for European Application No. 20857028.3, Search completed Aug. 11, 2023, dated Aug. 21, 2023, 12 pgs.
Extended European Search Report for European Application No. 23154548.4, Search completed Jun. 15, 2023, dated Jun. 23, 2023, 11 pgs.
International Preliminary Report on Patentability for International Application PCT/US2019/013870 Report dated Jul. 21, 2020, dated Jul. 30, 2020, 5 pgs.
International Preliminary Report on Patentability for International Application PCT/US2020/047054, Report dated Feb. 17, 2022, dated Mar. 3, 2022, 6 pgs.
International Preliminary Report on Patentability for International Application PCT/US2020/056354, Report dated Apr. 19, 2022, dated Apr. 28, 2022, 6 pgs.
International Preliminary Report on Patentability for International Application PCT/US2021/072678, Report dated May 30, 2023, dated Jun. 15, 2023, 9 pgs.
International Search Report and Written Opinion for International Application No. PCT/US2019/013870, Search completed Mar. 18, 2019, dated Mar. 27, 2019, 9 pgs.
International Search Report and Written Opinion for International Application No. PCT/US2020/047054, Search completed Oct. 8, 2020, dated Nov. 23, 2020, 10 pgs.
International Search Report and Written Opinion for International Application No. PCT/US2020/056354, Search completed Dec. 21, 2020, dated Jan. 25, 2021, 9 pgs.
International Search Report and Written Opinion for International Application No. PCT/US2022/073165, Search completed Aug. 14, 2022, dated Sep. 7, 2022, 9 pgs.
International Search Report and Written Opinion for International Application No. PCT/US2023/069016, Search completed Sep. 18, 2023, dated Oct. 18, 2023, 11 pgs.
International Search Report and Written Opinion for International Application No. PCT/US2023/070276, Search completed Oct. 6, 2023, dated Nov. 8, 2023, 16 pgs.
International Search Report and Written Opinion for International Application PCT/US2021/072678, search completed Jan. 31, 2022, dated Jul. 1, 2022, 13 pgs.
"PROCOVA™ Handbook for the Target Trial Statistician", Ver. 1.0, European Medicines Agency, Dec. 29, 2021, 7 pgs.
Ackley et al., "A learning algorithm for boltzmann machines", Cognitive Science, vol. 9, No. 1, 1985, pp. 147-169.
Akhtar et al., "Improving the Robustness of Neural Networks Using K-Support Norm Based Adversarial Training", IEEE Access; Publication [online]. Dec. 28, 2016, 10 pgs.
Allison et al., "Handling Missing Data by Maximum Likelihood", SAS Global Forum 2012: Statistics and Data Analysis, 21 pgs.
Amin et al., "Quantum Boltzmann Machine", [retrieved on Jun. 10, 2023]. Retrieved from the Internet: <URL:https://journals.aps.org/prx/pdf/10.1103/PhysRevX.8.021050>, May 23, 2018, pp. 021050-1 to 021050-11.
Arici et al., "Associative Adversarial Networks", arXiv:1611.06953v1 [cs.LG], Nov. 18, 2016, 8 pgs. URL:https://arxiv.org/abs/1611.06953.
Arjovsky et al., "Wasserstein GAN", arXiv:1701.07875v1 [stat.ML], Jan. 26, 2017, 30 pgs.
Balzer et al., "Adaptive pair-matching in randomized trials with unbiased and efficient effect estimation", Statistics in Medicine, 2015, vol. 34, pp. 999-1011.
Bengio et al., "Greedy Layer-Wise Training of Deep Networks", Advances in Neural Information Processing Systems, 2007, 13 pgs.
Burges et al., "Learning to Rank Using Gradient Descent", Proceedings of the 22nd International Conference on Machine Learning, 2005, 8 pgs.
Chatterjee et al., "Explaining Complex Distributions with Simple Models", 2008. Econophysics, pp. 1-15.
Cho et al., "Gaussian-Bernoulli deep Boltzmann machine", Proceedings of the 2013 International Joint Conference on Neural Networks (IJCNN), Dallas, Texas, Aug. 4-9, 2013, 9 pgs.
Coon et al., "A High-Density Whole-Genome Association Study Reveals That APOE Is the Major Susceptibility Gene for Sporadic Late-Onset Alzheimer's Disease", The Journal of Clinical Psychiatry, 2007, vol. 68, No. 04, 2007, pp. 613-618, doi: 10.4088/jcp.v68n0419.
Cui et al., "Multilevel Modeling and Value of Information in Clinical Trial Decision Support", BMC Systems Biology (2014) 8:6, 8 pgs. DOI 10.1186/s12918-014-0140-0.
Davidian et al., "Semiparametric Estimation of Treatment Effect in a Pretest-Posttest Study with Missing Data", statistical Science, vol. 20, No. 3, pp. 261-301.
Dutt et al., "Generative Adversarial Networks (GAN) Review", CVR Journal of Science and Technology, Dec. 2017, vol. 13, pp. 1-5.
Eickhoff et al., "Copulas for Information Retrieval", Proceedings of the 36th International ACM SIGIR Conference on Research and Development in Information Retrieval, Jul. 2013, pp. 663-672.
Fisher et al., "Boltzmann Encoded Adversarial Machines", arxiv.org:1804.08682v1, Apr. 23, 2018, XP081229135, 17 pgs.
Fisher et al., "Machine learning for comprehensive forecasting of Alzheimers disease progression", Scientific Reports, vol. 9, No. 1, 2019, 14 pgs.
Gabrie et al., "Training Restricted Boltzmann Machines via the Thouless-Anderson-Palmer Free Energy", Advances in Neural Information Processing Systems, vol. 28, 2015, 9 pgs.
Ghojogh et al., "Restricted Boltzmann Machine and Deep Belief Network: Tutorial and Survey", arXiv preprint arXiv:2107.12521, 2022, 16 pgs.
Goodfellow et al., "Generative Adversarial Nets", arXiv:1406.2661v1 [stat.ML], Jun. 10, 2014, 9 pgs.
Goodfellow et al., "Multi-Prediction Deep Boltzmann Machines", [retrieved on Jun. 10, 2023]. Retrieved from the Internet: <URL:https://proceedings.neurips.cc/paper/2013/file/0bb4aec1710521c12ee76289d9440817-Paper.pdf> Dec. 5, 2013, pp. 1-9.
Graham et al., "Analysis with missing data in drug prevention research", NIDA Research Monograph, Feb. 1994, vol. 142, pp. 325-366.
Greydanus, "Generative Adversarial Networks for the MNIST dataset", "Mnist gan," http://github.com/greydanus/mnist-gan (2017), 2 pgs.
Grover et al., "Flow-GAN: Combining Maximum Likelihood and Adversarial Learning in Generative Models", arXiv:1705.08868v2, Jan. 3, 2018, 10 pgs.
Gupta, "Intention-to-treat concept: a review", Perspectives in Clinical Research, Jul. 2011, vol. 2, No. 3, pp. 109-112, doi: 10.4103/2229-3485.83221.
Hannan, "Randomized Clinical Trials and Observational Studies: Guidelines for Assessing Respective Strengths and Limitations", JACC: Cardiovascular Interventions, Jun. 2008, vol. 1, No. 3, pp. 211-217, https://doi.org/10.1016/j.jcin.2008.01.008.
Herlau et al., "Bayesian Dropout", arXiv e-prints (2015): arXiv-1508.02905v1, 21 pages.
Hinton, "A Practical Guide to Training Restricted Boltzmann Machines", University of Toronto, Technical Report UTML TR 2010-003, 2010, 21 pages. <URL: http://www.cs.toronto.edu/ hinton/absps/guideTR.pdf>.
Hinton et al., "A Fast Learning Algorithm for Deep Belief Nets", Neural Computation, vol. 18, 2006, pp. 1527-1554.
Hinton et al., "Reducing the Dimensionality of Data with Neural Networks", Science, vol. 313, No. 5786, Jul. 28, 2006, pp. 504-507.
Hinton et al., "Training products of experts by minimizing contrastive divergence", Neural Computation, vol. 14, No. 8, 2002, pp. 1771-1800.
Hoffman et al., "Training Compute-Optimal Large Language Models", arXiv preprint arXiv:2203.15556, 2022, 36 pgs.
Jerez et al., "Missing data imputation using statistical and machine learning methods in a real breast cancer problem", Artificial Intelligence in Medicine, (Year: 2010), vol. 50, Issue 2, pp. 105-115.
Karcher et al., "The "RCT augmentation": a novel simulation method to add patient heterogeneity into phase III trials", BMC (56) References Cited

OTHER PUBLICATIONS

Medical Research Methodology (2018) 18:75; https://doi.org/10.1186/s1287 4-018-0534-6, 15 pgs.
Kim et al., "Deep Directed Generative Models with Energy-Based Probability Estimation", arXiv:1606.03439, Jun. 10, 2016, 9 pages. <URL: https : //arxiv.org/abs/1606. 03439>.
Kullback et al., "On Information and Sufficiency", The Annals of Mathematical Statistics, vol. 22, No. 1, 1951, pp. 79-86.
Lamb et al., "GibbsNet: Iterative Adversarial Inference for Deep Graphical Models", arXiv preprint arXiv:1712.04120v1, 2017, 11 pgs.
Li et al., "Temperature based Restricted Boltzmann Machines", Scientific Reports Jan. 13, 2016, vol. 19133, 12 pgs. DOI:10.1038/srep19133.
Liao et al., "Gaussian-Bernoulli RBMs Without Tears", arXiv preprint arXiv:2210.10318, 2022, 18 pgs.
Lipton et al., "Modeling Missing Data in Clinical Time Series with RNNs", Machine Learning for Healthcare. Jun. 13, 2016, vol. 56, 17 pgs.
Liu et al., "A Survey of Deep Neural Network Architectures and their Applications", Neurocomputing, Apr. 19, 2017, vol. 234, pp. 11-26, XP029916222, ISSN: 0925-2312, DOI: 0.1016/J.NEUCOM. 2016.12.038.
Liu et al., "Image inpainting for irregular holes using partial convolutions", Image Inpainting for Irregular Holes Using Partial Convolutions, Proceedings of the European conference on computer vision (ECCV), arXiv:1804.07723, 2018, 23 pgs.
Lopez-Ruiz et al., "Equiprobability, Entropy, Gamma Distributions and Other Geometrical Questions in Multi-Agent Systems", Entropy, 2009, vol. 11, pp. 959-971, doi:10.3390/e11040959.
Maldonado, "Estimating causal effects", International Journal of Epidemiology, Apr. 2002, vol. 31, No. 2, pp. 422-429.
Marlin et al., "Recommender systems: Missing Data and statistical Model Estimation", Proceedings of the Twenty-Second international joint conference on Artificial Intelligence, 2011, vol. Three (IJCAI'11), AAAI Press, pp. 2686-2691.
Melchior et al., "Gaussian-Binary Restricted Boltzmann Machines for Modeling Natural Image Statistics", PLOS One, vol. 12, No. 2, 2017, pp. 1-24.
Miotto et al., "Deep Learning for Healthcare: Review, Opportunities and Challenges", Briefings in Bioinformatics, May 6, 2017 (May 6, 2017), vol. 19, No. 6, pp. 1236-1246, GB ISSN: 1467-5463, DOI: 10.1093/bib/bbx044.
Mnih et al., "Conditional restricted Boltzmann machines for structured output prediction", arXiv preprint arXiv: 1202.3748, 2012, 9 pgs.
Montavon et al., "Wasserstein Training of Restricted Boltzmann Machines", Advances in Neural Information Processing Systems, vol. 29, 2016, 9 pgs.
Nakkiran et al., "Deep Double Descent: Where Bigger Models and More Data Hurt", arXiv preprint, arXiv:1912.02292, 2019, 24 pgs.
Neville et al., "Development of a unified clinical trial database for Alzheimer's disease", Alzheimer's & Dementia: The Journal of the Alzheimer's Association, 2015, vol. 11, No. 10, pp. 1212-1221, https://doi.org/10.1016/j.jalz.2014.11.005.
Mandel et al., "Autotagging music with conditional restricted Boltzmann machines", arXiv: 1103.2832; (Year: 2011), https://doi.org/10.48550/arXiv.1103.2832, 14 pgs.
Takayuki, "Boltzmann Machines for Time-Series", IBM Research—Tokio; 2019; arXiv:1708.06004v3 [cs.NE], 33 pgs.

\* cited by examiner

SYSTEMS AND METHODS ENABLING BASELINE PREDICTION CORRECTION

CROSS-REFERENCE TO RELATED APPLICATIONS

The current application claims the benefit of and priority under 35 U.S.C. § 119(e) to U.S. Provisional Patent Application No. 63/485,771 entitled "Baseline Predictor Corrector" filed Feb. 17, 2023. The disclosure of U.S. Provisional Patent Application No. 63/485,771 is hereby incorporated by reference in its entirety for all purposes.

FIELD OF THE INVENTION

The present invention generally relates to data analysis and application and, more specifically, time-series forecasting.

BACKGROUND

Time-series forecasting refers to computational trend analysis methods that are frequently used to make informed decisions, respond to environmental changes, and determine responses for industries such as healthcare and research. Time series forecasting generally involves making long-term predictions based on historical analysis and assessments of change over time. Time-series forecasting methods include recursive forecasting and direct multi-step forecasting, both of which carry their own benefits. Recursive forecasting is a method where predictions for future time steps are made one step at a time, using information (including other, earlier, forecasts) from previous time steps. In such cases, a single time series model is estimated, while the input for the next timestep is the output for the previous timestep, thereby functioning in a manner both conceptually simple and data efficient. Direct multi-step forecasting, on the other hand, involves using all observed/historical information to make predictions for multiple future time steps in one go. By training a model in full for multiple time steps, the approach avoids the accumulation of errors and leads to predictions with lower bias.

SUMMARY OF THE INVENTION

Systems and techniques for time-series forecasting are illustrated. One embodiment includes a method for refining time-series forecasts, the method obtains timestep information concerning a multivariate time-series generated for a system. The timestep information includes baseline information, a time gap, and context information. The baseline information includes information known about the system at a time when the multivariate time-series is generated. The context information includes at least one vector of time-independent background variables related to the system. The method determines, based on the timestep information, parameter predictions for the system at a first timestep and a second timestep, wherein the second timestep occurs after the first timestep and a time difference between the first timestep and the second timestep corresponds to the time gap. The method derives actual state values for the system at the first timestep. The method updates the parameter predictions for the system at the second timestep, using a gating function, based on a discrepancy between: the parameter predictions for the system at the first timestep, and the actual state values for the system at the first timestep.

In a further embodiment, the parameter predictions are selected from the group consisting of: predictions for a state of the system; and predictions for a variance of the system.

In a still further embodiment, when the parameter predictions are predictions for the state of the system, updating the parameter predictions is performed using the formula: $y_{t+dt}+(x_t-y_t)e^{-\lambda dt}$. In the formula, $\lambda$ corresponds to an array of learnable parameters; $dt$ corresponds to the time gap; $x_t$ corresponds to the actual state values for the system at the first timestep; $y_t$ corresponds to predictions for the state of the system at the first timestep; and $y_{t+dt}$ corresponds to predictions for the state of the system at the second timestep.

In another embodiment, when the parameter predictions are predictions for the variance of the system, updating the parameter predictions is performed using the formula: $(1-e^{-\lambda 2dt})s_{t+dt}^2$. In the formula, $\lambda$ corresponds to an array of learnable parameters; $dt$ corresponds to the time gap; and $s_{t+dt}^2$ corresponds to predictions for the variance of the system at the second timestep.

In yet another embodiment, updating the predictions for the variance of the system at the second timestep involves application of a softplus activation function.

In still yet another embodiment, the system corresponds to an experimental assessment, the multivariate time-series corresponds to a set of states of participants to the experimental assessment, and the baseline information includes data to be monitored in the experimental assessment.

In a further embodiment, each of the actual state values for the system correspond to observations for one or more participants to the experimental assessment, and each of the parameter predictions for the system correspond to predictions for one or more participants to the experimental assessment.

In another embodiment, the system corresponds to an assessment of a condition of a patient.

In still another embodiment, the multivariate time-series corresponds to a health history of the patient.

In a further embodiment, each of the actual state values for the system correspond to observations for one or more participants to the experimental assessment.

In another further embodiment, each of the parameter predictions for the system correspond to predictions for one or more participants to the experimental assessment.

In yet another embodiment, the baseline information includes information used in a recent diagnosis of the patient.

In still yet another embodiment, at least one of the parameter predictions for the system is applied to a medical diagnosis of the patient.

In another embodiment, the system corresponds to an assessment of a condition of a patient.

In a further embodiment, the multivariate time-series corresponds to a health history of the patient.

In another further embodiment, the baseline information includes information used in a recent diagnosis of the patient.

In yet another further embodiment, at least one of the parameter predictions for the system is applied to a medical diagnosis of the patient.

In another embodiment, parameter predictions for the system are determined by a neural network with learnable parameters.

In a further embodiment, the neural network is at least one of the group consisting of: a multilayer perceptron (MLP); and a residual neural network.

In a still further embodiment, the MLP includes a single linear layer.

In another embodiment the neural network takes, as a particular input, at least one from the group consisting of: a product of variables of the baseline information and time, and a product of variable of the context information and time.

In a further embodiment, the neural network automatically learns the particular input.

In another embodiment, the baseline information reflects a state of the system at a pre-determined point in the multivariate time-series.

In another embodiment, updating the parameter predictions for the system at the second timestep is further based on the time gap.

In a further embodiment, a determined length of the time gap is inversely proportional to weight given to the discrepancy in updating the parameter predictions for the system at the second timestep.

In another embodiment, the parameter predictions are anchored to the baseline information.

In still another embodiment, updating the parameter predictions for the system at the second timestep includes producing an adjustment term, wherein the adjustment term includes the gating function and the discrepancy, and In a further embodiment, updating the parameter predictions for the system at the second timestep includes adding the adjustment term to the parameter predictions for the system at the second timestep.

In another further embodiment, producing the adjustment term includes multiplying the gating function by the discrepancy.

In another embodiment, the method, when the discrepancy suggests that the parameter predictions for the first timestep is an underestimation, updates the parameter predictions for the second timestep includes increasing the parameter predictions for the second timestep.

In a further embodiment, the method, when the discrepancy suggests that the parameter predictions for the first timestep is an overestimation, updates the parameter predictions for the second timestep includes decreasing the parameter predictions for the second timestep.

In another embodiment, updating the parameter predictions for the system is performed on a recursive basis.

In yet another embodiment, the time-independent background variables include at least one selected from the group consisting of race, sex, disability, and genetic profile.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Turning now to the drawings, systems and methods configured in accordance with various embodiments of the invention may enable precise, low-latency forecasting for fields including but not limited to healthcare diagnosis, treatment, and/or research. Systems configured in accordance with some embodiments of the invention may be referred to as Baseline Predictor-Correctors in this application. Many problems (e.g., modeling patient trajectories) require the ability to generate time-series. That is, to generate a sequence of states $\{v(t)\}_{t=0}^{\tau}$. Baseline Predictor-Correctors configured in accordance with many embodiments can incorporate predictor models (f) to provide best guess predictions at two or more time-series time points (t, t+dt) based on information including but not limited to previous timestep state estimates, observed information, and baseline information ($x_0$) (i.e., information known before any forecasting is performed). Additionally or alternatively, best guess predictions may depend on static context information including but not limited to time-independent background variables. Once best guess predictions are obtained systems may utilize corrector models (h) to adjust the predictor based on variables including but not limited to the change in time (dt) and values derived from discrepancies between the estimated change(s) and the observed change(s).

Figure 1:
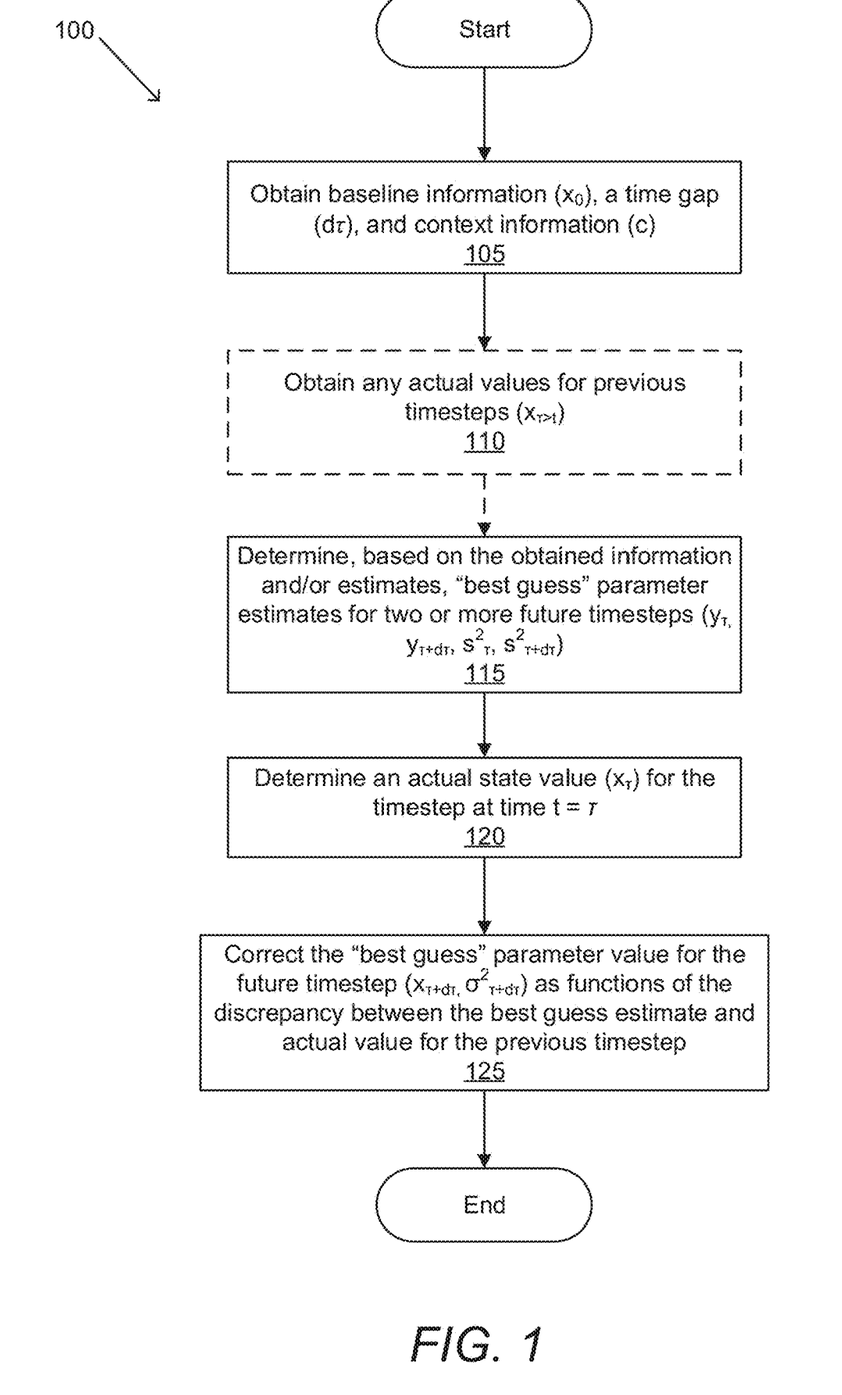
FIG. 1 conceptually illustrates a process for deriving and updating a time-series forecast generated in accordance with many embodiments of the invention.

A process for deriving and updating a time-series forecast generated in accordance with many embodiments of the invention, is illustrated in FIG. 1. Process 100 obtains (105) baseline information ($x_0$), a time gap ($d\tau$), and context information (c). In accordance with certain embodiments of the invention, context information may take the form of vectors of time-independent background variables. Within healthcare and/or clinical trials, context information may include but is not limited to pre-treatment covariates such as race, sex, disability, and/or genetic profile. Additionally or alternatively baseline information may incorporate various types of information known before and/or at the start of forecasting attempts. In particular, such characteristics may be used to answer, through time-series configured in accordance with some embodiments, inquiries such as "Given a subject's baseline characteristics, how will those characteristics evolve in time?" As such, in accordance with some embodiments, baseline information for individual clinical trials may include but is not limited to T-cell count, bone density, and/or BMI.

Process 100 may also obtain (110) any actual state values for previous timesteps ($x_{\tau>t}$), wherein the actual state values reflect the state of the system being forecast. In accordance with many embodiments of the invention, ($x_\tau$, $\tau>0$) may disclose soon-to-be observed states, that correspond to time t=$\tau$>0. As such, the time gap (d$\tau$) may refer to the difference in time between time t=$\tau$ and the time that is to be observed further in the future, ($\tau$+d$\tau$; $\tau$>0; d$\tau$>0). In accordance with some embodiments, observed states may correspond to one or more trial participants.

Process 100 determines (115), based on the obtained information and/or actual values, "best guess" parameter estimates for two or more future timesteps. In accordance with numerous embodiments of the invention, parameters may include but are not limited to state estimates (also referred to as "expected values" in this disclosure) and/or variance estimates ($x_\tau$, $x_{\tau+d\tau}$, $\sigma_\tau^2$, $\sigma_{\tau+d\tau}^2$). Best guess parameters may be produced by predictor models ("predictors"). In accordance with multiple embodiments, predictors (e.g., $f_1$, $f_2$) may provide best guess parameters including but not limited to state and/or variance estimates for time t=$\tau$ and/or time t=$\tau$+d$\tau$ conditioned on the baseline ($x_0$) and context (c) information and/or the various previous timestep information available. This may enable best guess parameters including but not limited to best guesses for expected values, i.e., state estimates ($y_t$):

$$y_\tau := f_1(x_0, c, \tau) \approx E[x_\tau | x_0, c, \tau]$$

$$y_{\tau+d\tau} := f_1(x_0, c, \tau+d\tau) \approx E[x_{\tau+d\tau} | x_0, c, \tau+d\tau] \quad (1A)$$

and best guesses for variance ($s_t^2$):

$$s_\tau^2 := f_2(x_0, c, \tau) \approx \mathrm{Var}[x_\tau | x_0, c, \tau]$$

$$s_{\tau+d\tau}^2 := f_2(x_0, c, \tau+d\tau) \approx \mathrm{Var}[x_{\tau+d\tau} | x_0, c, \tau+d\tau] \quad (1B)$$

Process 100 determines (120) an actual state value (e.g., $x_\tau$) for the timestep at time $t=\tau$. In accordance with various embodiments of the invention, once the actual state value for time $t=\tau$ is obtained (120), comparisons to the best guess state estimates ($y_\tau$) for time $t=\tau$ may be generated. Additionally or alternatively, comparisons to other best guess parameters, including but not limited to variance ($s_\tau^2$) for time $t=\tau$ may be generated.

Process 100 corrects (125) the "best guess" parameter estimates for the future timestep (e.g., $y_{\tau+d\tau}$; $s_{\tau+d\tau}^2$) as functions of the discrepancy between the state estimate and the actual state value for the previous timestep. As indicated above, these corrections may be performed on, but are not limited to state estimates ($y_{\tau+d\tau}$) and/or variance estimates ($s_{\tau+d\tau}^2$) Corrector models ("correctors") may be used to correct the best guess at time $\tau+d\tau$ using the actual information from the previous time step $x_\tau$. In accordance with various embodiments, when the prediction of the predictor f is undershooting the actual state values at time $\tau$, correctors ($h_1$, $h_2$) may conclude a high likelihood that f will undershoot state estimate $y_{\tau+d\tau}$. In such instances, h may determine that the output should be a positive contribution. Additionally or alternatively, when predictor f overshoots at time $\tau$ then h may conclude a high likelihood that f will overshoot state estimates (e.g., $x_{\tau+d\tau}$ will overshoot $y_{\tau+d\tau}$; $s_{\tau+d\tau}^2$ will overshoot $\sigma_{\tau+d\tau}^2$)

The final prediction may then take the form:

$$E[x_{\tau+d\tau} | x_0, x_\tau, \tau, d\tau, c] \approx h_1(y_\tau, y_{\tau+d\tau}, s_\tau^2, s_{\tau+d\tau}^2, x_\tau, d\tau) \quad (2A)$$

$$\mathrm{Var}[x_{\tau+d\tau} | x_0, x_\tau, \tau, d\tau, c] \approx h_2(y_\tau, y_{\tau+d\tau}, s_\tau^2, s_{\tau+d\tau}^2, x_\tau, d\tau) \quad (2B)$$

wherein $h_{(\cdot)}(y_\tau, y_{\tau+d\tau}, s_\tau^2, s_{\tau+d\tau}^2, x_\tau, d\tau)$ represents the corrector model configuration. As such, the correctors may update estimates based on inputs including but not limited to initial best guess parameter estimates for the two or more timesteps $\tau$ ($y_\tau, s_\tau^2$) and $\tau+d\tau(y_{\tau+d\tau}, s_{\tau+d\tau}^2)$ actual state values for timestep $\tau$ ($x_\tau$), and/or time lags between the timesteps ($d\tau$). In accordance with various embodiments of the invention, the outputs of the correctors may thereby be consistent.

In accordance with many embodiments of the invention, correctors may, additionally or alternatively, depend on time gap(s) $d\tau$. When time gaps are very large, correctors may determine that discrepancies at time $\tau$ have less weight in regards to how the correction should be applied at $\tau+d\tau$. In such cases, systems configured in accordance with numerous embodiments of the invention may, as $d\tau$ passes above a certain threshold, determine that predictions for parameters at timestep at $\tau+d\tau$ can be effectively reduced to the initial best estimates. When this happened:

$$E[x_{\tau+d\tau} | x_0, x_\tau, \tau, d\tau, c] \approx y_{\tau+d\tau} \quad (3A)$$

$$\mathrm{Var}[x_{\tau+d\tau} | x_0, x_\tau, \tau, d\tau, c] \approx s_{\tau+d\tau}^2 \quad (3B)$$

Additionally or alternatively, when $d\tau$ is small, correctors may determine that discrepancies at time $\tau$ have more weight in regards to how the correction which should be applied at $\tau+d\tau$. In such cases, systems configured in accordance with many embodiments of the invention may, as $d\tau$ passes under a particular threshold, determine that predictions for parameters at timestep at $\tau+d\tau$ can be adjusted. In particular, in such cases, the resulting formulae may take the form:

$$E[x_{\tau+d\tau} | x_0, x_\tau, \tau, d\tau, c] \approx x_\tau$$

$$\mathrm{Var}[x_{\tau+d\tau} | x_0, x_\tau, \tau, d\tau, c] < \min(s_{\tau+d\tau}^2, s_\tau^2) \quad (4A)$$

Systems and methods configured in accordance with a number of embodiments of the invention can be applied recursively to generate long-term forecasts. At each recursion step, the predictions may be anchored to the baseline information thus preventing the accumulation of errors. By using the information available at the previous timestep, systems may generate long forecasts with precise time-correlation between timesteps.

In accordance with certain embodiments of the invention, for the first recursion step, $x_\tau$ may be unknown. In response to this, systems configured in accordance with many embodiments may follow Equations (1A) and (1B). Additionally or alternatively, systems configured in accordance with certain embodiments may set $\tau=0$ such that $x_\tau=y_\tau=x_0$.

In accordance with some embodiments of the invention, predictive inferences made by predictors may take various forms. Predictors may operate as deterministic functions of their respective input values. In accordance with numerous embodiments, predictors can be implemented as Neural Networks with learnable parameters. Additionally or alternatively, predictors can be implemented as Multilayer perceptrons (MLPs). For example, certain predictors for state estimators (h) may follow the equation:

$$y_t = f_1(x_0, c, t) = \mathrm{MLP}(x_0, c, t \times x_0, t \times c, t) \quad (5A)$$

In accordance with certain embodiments, MLP predictors may receive, as input features, the product of baseline and context variables with time ($t \times x_0$, $t \times c$) in addition to the original variables.

In accordance with many embodiments of the invention, various types of feature engineering, including the above may be implemented by MLPs. For example, in accordance with numerous embodiments, predictors can be implemented as residual neural networks. For example, predictors for state estimates may follow the equation:

$$y_t = f_1(x_0, c, t) = x_0 + \mathrm{MLP}(t \times x_0, t \times c, t) \quad (5B)$$

In accordance with many embodiments, predictors for variance ($f_2$) may include non-linearities including but not limited to softplus activation functions in order to enforce non-negative outputs. As such, predictors for variance estimates may follow the equation:

$$s_t^2 = f_2(x_0, c, t) = \mathrm{activation}(\mathrm{MLP}(x_0, c, t \times x_0, t \times c, t)) \quad (6A)$$

Additionally or alternatively, predictors for variance may follow the equation:

$$s_t^2 = f_2(x_0, c, t) = \mathrm{activation}(a(x_0, c) + b(x_0, c) \times t) \quad (6B)$$

where a and b are non-negative learnable functions. In accordance with numerous embodiments, non-negative learnable functions can be implemented as, but are not limited to, MLPs. Additionally or alternatively, activation functions may be used here to control and/or cap variance growth over time.

In accordance with some embodiments of the invention, MLP predictors may be configured to automatically learn derived features including but not limited to the product(s) of baseline and context variables with time. Additionally or alternatively, systems may directly provide such variables to enable the use of shallower networks, improving training and which results in faster training and less over-fitting. In accordance with a few embodiments, MLPs can be reduced to single linear layers.

In accordance with many embodiments of the invention, corrections made by correctors may take numerous forms. In particular, corrector functions may need to be considered in tandem, due to prospective consistency requirements described above. In accordance with some embodiments, correctors can be implemented as gating functions. Additionally or alternatively, the gating function may be multiplied by discrepancies between actual state values and best guesses (e.g. $(x_t - y_t)$).

In accordance with certain embodiments, correctors for state estimates may utilize various gating functions that input variables including but not limited to state estimates (e.g., $y_t, y_{t+dt}$), variance best guesses (e.g., $s_t^2, s_{t+dt}^2$), actual state values (e.g., $x_t$) and/or time gaps (e.g., dt). For example, so correctors for state estimates may take the form:

$$h_1(y_t, y_{t+dt}, s_t^2, s_{t+dt}^2, x_t, dt) = y_{t+dt} + (x_t - y_t)e^{-\lambda dt} \quad (7)$$

wherein $\lambda$ represents an array of learnable parameters. In accordance with various embodiments of the invention, gating functions (e.g., $e^{-\lambda dt}$) may depend on time gaps to reflect system expectations that, as dt increases, correction inferences will decrease to zero. Gating functions for state estimates configured in accordance with certain embodiments may interpolate between short time lag situations (e.g., where dt approaches 0 and $h_1 \approx x_t$) and long time lag situations (e.g., where dt approaches $\infty$ and $h_1 \approx y_{t+dt}$). As such, discrepancies (at timestep t) between predictions and actual values may be modified accordingly.

In accordance with numerous embodiments, the corrector for state estimates may pose constraints on the form of correctors for other parameters, including but not limited to variance. Gating functions for variance configured in accordance with multiple embodiments may similarly interpolate between short time lag situations (e.g., where dt approaches 0 and $h_2 \approx 0$) and long time lag situations (e.g., where dt approaches $\infty$ and $h_2 \approx s_{t+dt}^2$). For example, one such version of the gating function for variance correctors may be:

$$h_2(y_t, y_{t+dt}, s_t^2, s_{t+dt}^2, x_t, dt) = (1 - e^{-\lambda 2 dt})s_{t+dt}^2 \quad (8)$$

which can enable $h_2$ to remain non-negative.

While specific processes for generating time-series forecasts are described above, any of a variety of processes can be utilized to forecast time-series as appropriate to the requirements of specific applications. In certain embodiments, steps may be executed or performed in any order or sequence not limited to the order and sequence shown and described. In a number of embodiments, some of the above steps may be executed or performed substantially simultaneously where appropriate or in parallel to reduce latency and processing times. In some embodiments, one or more of the above steps may be omitted.

Figure 2:
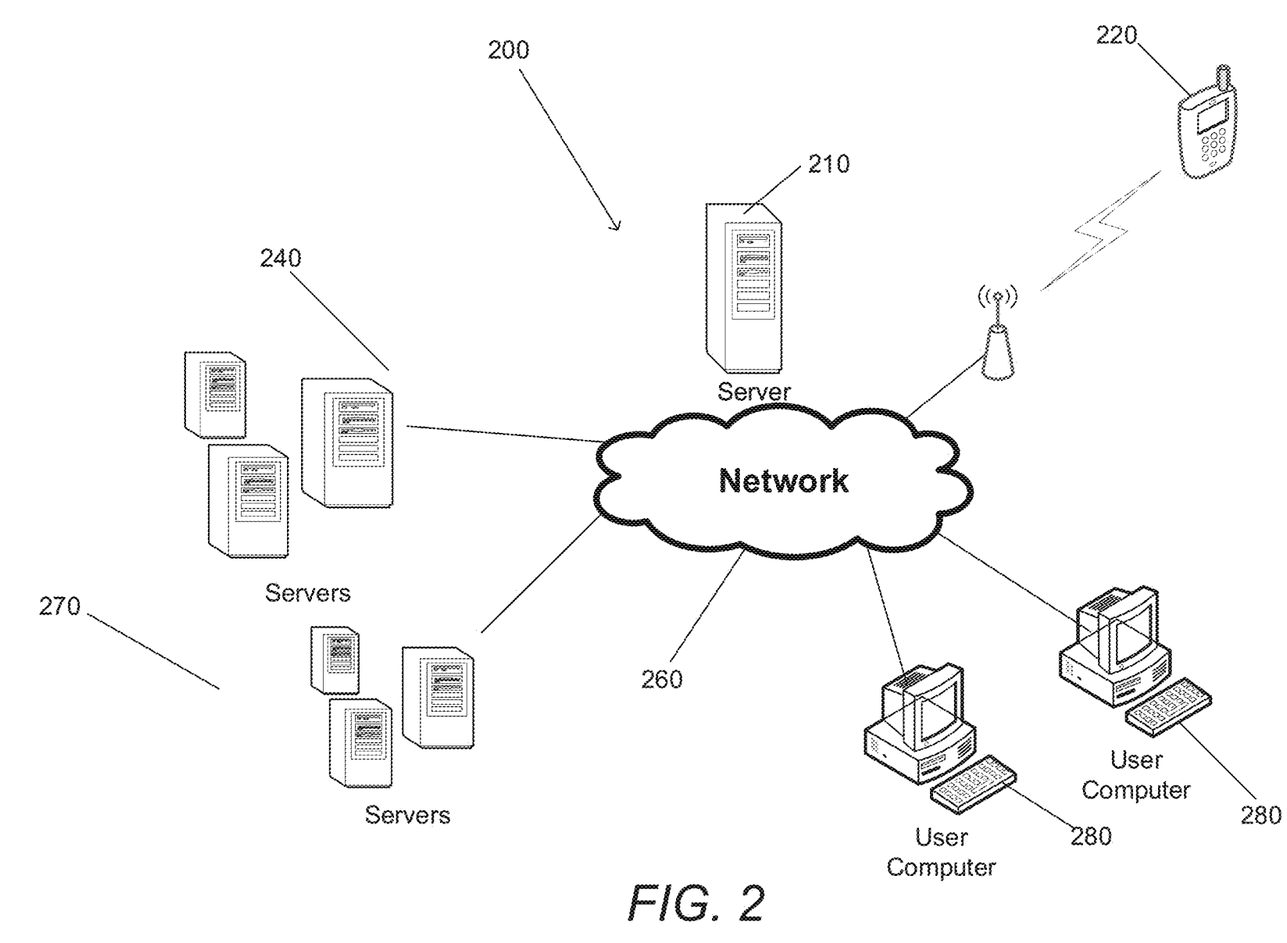
FIG. 2 illustrates a system that provides for the gathering and distribution of data for producing time-series forecasts in accordance with numerous embodiments of the invention.

A system that provides for the gathering and distribution of data for forecasting time-series in accordance with some embodiments of the invention is shown in FIG. 2. Network 200 includes a communications network 260. The communications network 260 is a network such as the Internet that allows devices connected to the network 260 to communicate with other connected devices. Server systems 210, 240, and 270 are connected to the network 260. Each of the server systems 210, 240, and 270 is a group of one or more servers communicatively connected to one another via internal networks that execute processes that provide cloud services to users over the network 260. For purposes of this discussion, cloud services are one or more applications that are executed by one or more server systems to provide data and/or executable applications to devices over a network. The server systems 210, 240, and 270 are shown each having three servers in the internal network. However, the server systems 210, 240 and 270 may include any number of servers and any additional number of server systems may be connected to the network 260 to provide cloud services. In accordance with various embodiments of this invention, a network that uses systems and methods that forecast and/or modified time-series in accordance with an embodiment of the invention may be provided by a process (or a set of processes) being executed on a single server system and/or a group of server systems communicating over network 260.

Users may use personal devices 280 and 220 that connect to the network 260 to perform processes for providing and/or interaction with a network that uses systems and methods that m in accordance with various embodiments of the invention. In the shown embodiment, the personal devices 280 are shown as desktop computers that are connected via a conventional "wired" connection to the network 260. However, the personal device 280 may be a desktop computer, a laptop computer, a smart television, an entertainment gaming console, or any other device that connects to the network 260 via a "wired" connection. The mobile device 220 connects to network 260 using a wireless connection. A wireless connection is a connection that uses Radio Frequency (RF) signals, Infrared signals, or any other form of wireless signaling to connect to the network 260. In FIG. 2, the mobile device 220 is a mobile telephone. However, mobile device 220 may be a mobile phone, Personal Digital Assistant (PDA), a tablet, a smartphone, or any other type of device that connects to network 260 via wireless connection without departing from this invention.

As can readily be appreciated the specific computing systems used to manage time-series applications are largely dependent upon the requirements of a given application and should not be considered as limited to any specific computing system(s) implementation.

Figure 3:
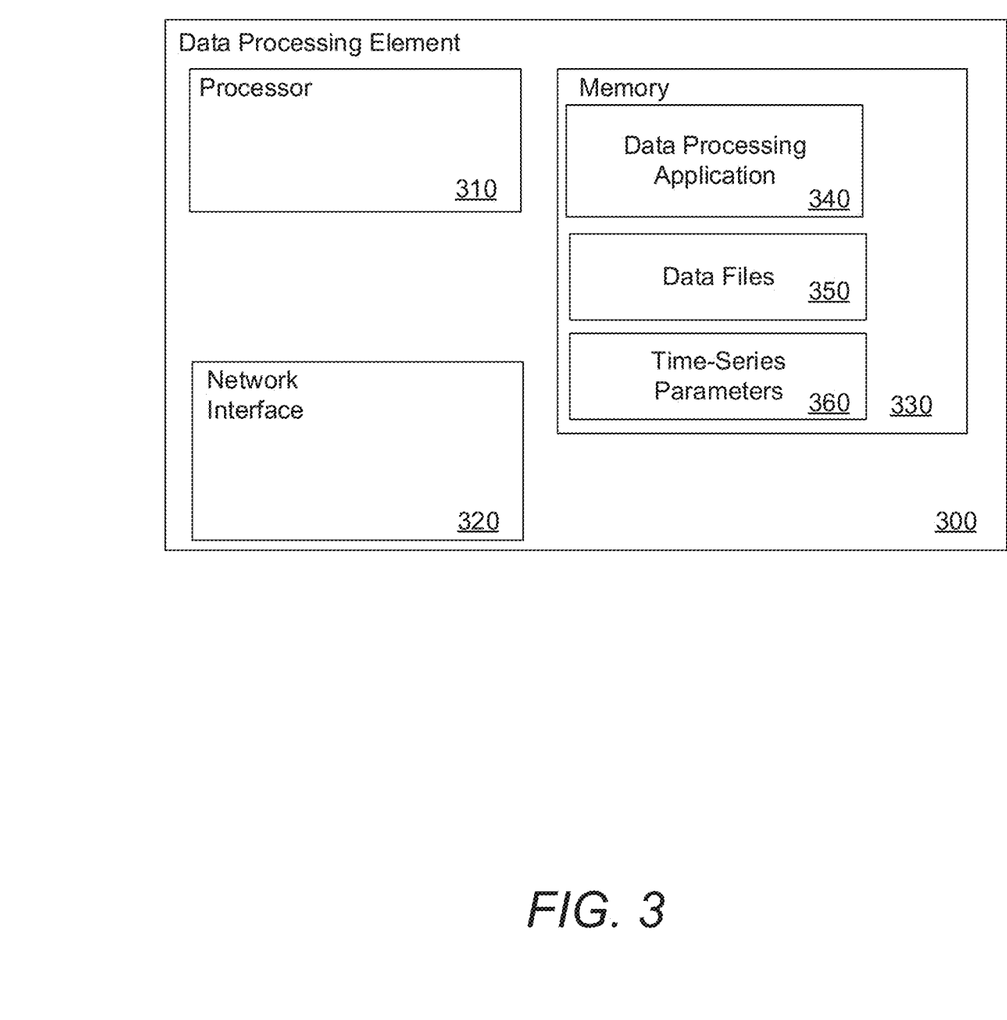
FIG. 3 illustrates a data processing element constructed in accordance with various embodiments of the invention.

An example of a data processing element for training and utilizing a generative model in accordance with a number of embodiments is illustrated in FIG. 3. In various embodiments, data processing element 300 is one or more of a server system and/or personal devices within a networked system similar to the system described with reference to FIG. 2. Data processing element 300 includes a processor (or set of processors) 310, network interface 320, and memory 330. The network interface 320 is capable of sending and receiving data across a network over a network connection. In a number of embodiments, the network interface 320 is in communication with the memory 330. In several embodiments, memory 330 is any form of storage configured to store a variety of data, including, but not limited to, a data processing application 340, data files 350, and time-series parameters 360. Data processing application 340 in accordance with some embodiments of the invention directs the processor 310 to perform a variety of processes, including but not limited to the process disclosed in FIG. 1. Processor 310 may use data from data files 350 to update time-series parameters 360 in order to allow the processor 310 to determine, update, and/or apply time-series forecasts in accordance with many embodiments of the invention.

Figure 4:
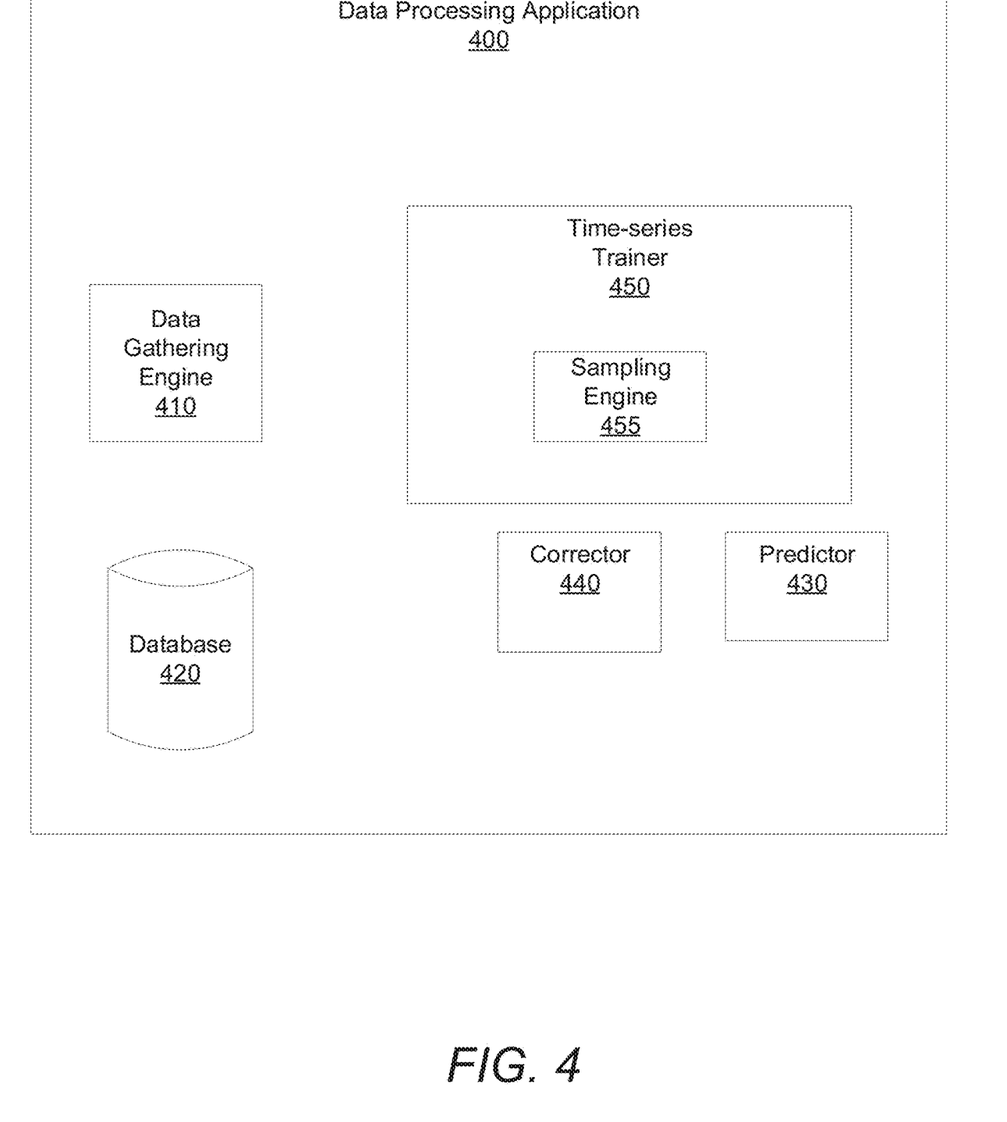
FIG. 4 illustrates a data processing application configured in accordance with certain embodiments of the invention.

A data processing application in accordance with a number of embodiments of the invention is illustrated in FIG. 4. In accordance with many embodiments of the invention, data processing applications 400 may be used to produce and/or modify time-series forecasts. In this example, data processing application 400 includes a data gathering engine 410, database 420, a predictor 430, a corrector 440, and a time-series trainer 450. The trainers 450 may include but are not limited to sampling engine(s) 455 which can be used to perform random sampling processes used in training predictors 430 and/or correctors 440. Data processing applications in accordance with many embodiments of the invention process data to generate and/or modify forecasts.

Databases in accordance with various embodiments of the invention store data for use by data processing applications, including (but not limited to) input data, pre-processed data, time-series parameters, and output data. In some embodiments, databases may be located on separate machines (e.g., in cloud storage, server farms, networked databases, etc.) from data processing applications.

As described above, as a part of the data-gathering process, the data in accordance with several embodiments of the invention may be pre-processed in order to simplify the data. Unlike other pre-processing which is often highly manual and specific to the data, this can be performed automatically based on the type of data, without additional input from another person.

Although specific examples of data processing elements and applications are illustrated in FIGS. 3-4, any of a variety of data processing elements and/or applications can be utilized to perform processes for facilitating time-series generation and modification similar to those described herein as appropriate to the requirements of specific applications in accordance with embodiments of the invention.

Even though it may only be possible to predict the probability of a health outcome for an individual patient, time-series configured in accordance with many embodiments of the invention can make it possible to precisely predict the number of patients with that health outcome in a large population. For example, predicting health risks may make it possible to accurately estimate the cost of insuring a population. Similarly, predicting the likelihood that a patient will respond to a particular therapeutic may make it possible to estimate the probability of a positive outcome in a clinical trial.

Developing the ability to accurately predict patients' prognoses is a necessary step towards precision medicine. A patient can be represented as a collection of information that describes their symptoms, their genetic information, results from diagnostic tests, any medical treatments they are receiving, and other information that may be relevant for characterizing their health. A vector containing this information about a patient may be described as a phenotype vector. A method for prognostic prediction in accordance with many embodiments of the invention uses past and current health information about a patient to predict a health outcome at a future time.

A patient trajectory, in accordance with numerous embodiments of the invention, may refer to time-series that describe patients' detailed health status(es) (e.g., a patient's phenotype vector) at various points in time. In several embodiments, prognostic prediction may take in a patient's trajectory (i.e., their past and current health information) and output predictions about a specific future health outcome (e.g., the likelihood they will have a heart attack within the next 2 years). By contrast, predicting a patient's future trajectory may involve predicting all of the information that characterizes the state of their health at all future times.

To frame this mathematically, let v(t) be a phenotype vector containing all of the information characterizing the health of a patient at time t. Therefore, a patient trajectory is a set $\{v(t)\}_{t=0}^{T}$. In some embodiments of the invention, models for simulating patient trajectories use discrete time steps (e.g., one month). Many of the examples are described with discrete time steps (e.g., τ=one month), but one skilled in the art will recognize that this is not necessary and that various other time steps can be employed in accordance with various embodiments of the invention. The length of the time step(s) in accordance with a number of embodiments of the invention may be selected to approximately match the frequency of treatment.

Additionally or alternatively, clinical decision support systems may provide information to patients, physicians, and/or other caregivers to help guide choices about patient care. Simulated patient trajectories may be applied to provide insights into a patient's future health that can inform choices of care. For example, a physician or caregiver can benefit from knowing the risks that a patient with mild cognitive impairment progresses to Alzheimer's disease, and/or that he or she begins to exhibit other cognitive or psychological systems. In certain embodiments, systems based on simulated patient trajectories can forecast these risks to guide care choices. Aggregating such predictions over a population of patients can also help estimate population level risks, enabling long-term planning by organizations, such as elder care facilities, that act as caregivers to large groups of patients. In some cases, models that are trained on data with treatment information would contain variables that describe treatment choices. Such a model could be used to assess how different treatment choices would change the patient's future risks by comparing simulated outcome risks conditioned on different treatments. In many embodiments, a caretaker or physician can treat a patient based on the treatment choices and/or the simulated trajectories.

Although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

The invention claimed is:

1. A method for refining time-series forecasts, the method comprising:
   obtaining timestep information concerning a multivariate time-series generated for a system, wherein:
      the timestep information comprises baseline information, a time gap, and context information,
      the baseline information comprises information known about the system at a time when the multivariate time-series is generated, and
      the context information comprises at least one vector of time-independent background variables related to the system;
   determining, based on the timestep information, parameter predictions for the system at a first timestep and a second timestep, wherein the second timestep occurs after the first timestep and a time difference between the first timestep and the second timestep corresponds to the time gap;
   deriving actual state values for the system at the first timestep; and
   updating the parameter predictions for the system at the second timestep, using a gating function, wherein:
      the parameter predictions comprise predictions for a state of the system; and updating the predictions for the state of the system comprises adding a term to the predictions for the state of the system, wherein the term is:
    inversely proportional to the time clap; and
    directly proportional to a discrepancy between:
        the parameter predictions for the system at the first timestep, and
        the actual state values for the system at the first timestep.

2. The method of claim 1, wherein the parameter predictions comprise predictions for a variance of the system.

3. The method of claim 2, wherein, updating the predictions for the state of the system is performed using formula: $y_{t+dt}+(x_t-y_t)e^{-\lambda dt}$, wherein:
    $\lambda$ corresponds to an array of learnable parameters;
    dt corresponds to the time gap;
    $x_t$ corresponds to the actual state values for the system at the first timestep;
    $y_t$ corresponds to predictions for the state of the system at the first timestep; and
    $y_{t+dt}$ corresponds to predictions for the state of the system at the second timestep.

4. The method of claim 2, wherein, when the parameter predictions comprise predictions for the variance of the system, updating the parameter predictions is performed using formula: $(1-e^{-\lambda 2 dt})s_{t+dt}^2$, wherein:
    $\lambda$ corresponds to an array of learnable parameters;
    dt corresponds to the time gap; and
    $s_{t+dt}^2$ corresponds to predictions for the variance of the system at the second timestep.

5. The method of claim 2, wherein updating the predictions for the variance of the system at the second timestep involves application of a softplus activation function.

6. The method of claim 1, wherein the system corresponds to an experimental assessment.

7. The method of claim 6, wherein the multivariate time-series corresponds to a set of states of participants to the experimental assessment.

8. The method of claim 6, wherein the baseline information comprises data to be monitored in the experimental assessment.

9. The method of claim 6, wherein each of the actual state values for the system correspond to observations for one or more participants to the experimental assessment.

10. The method of claim 6, wherein each of the parameter predictions for the system correspond to predictions for one or more participants to the experimental assessment.

11. The method of claim 1, wherein the system corresponds to an assessment of a condition of a patient.

12. The method of claim 11, wherein the multivariate time-series corresponds to a health history of the patient.

13. The method of claim 11, wherein the baseline information comprises information used in a recent diagnosis of the patient.

14. The method of claim 11, wherein at least one of the parameter predictions for the system is applied to a medical diagnosis of the patient.

15. The method of claim 1, wherein parameter predictions for the system are determined by a neural network with learnable parameters.

16. The method of claim 15, wherein the neural network is at least one of the group consisting of:
    a multilayer perceptron (MLP); or
    a residual neural network.

17. The method of claim 16, wherein the MLP comprises a single linear layer.

18. The method of claim 15, wherein the neural network takes, as a particular input, at least one from the group consisting of:
    a product of variables of the baseline information and time; or
    a product of variable of the context information and time.

19. The method of claim 18, wherein the neural network automatically learns the particular input.

20. The method of claim 1, wherein the baseline information reflects a state of the system at a pre-determined point in the multivariate time-series.

* * * * *